United States Patent [19]
Heinecke et al.

[11] Patent Number: 5,849,325
[45] Date of Patent: Dec. 15, 1998

[54] MOISTURE-REGULATING ADHESIVE DRESSING

[75] Inventors: Steven B. Heinecke, New Richmond, Wis.; Donald H. Lucast, North St. Paul; John T. Capecchi, Oakdale, both of Minn.

[73] Assignee: Minnesota Mining and Manufacturing Company, St. Paul, Minn.

[21] Appl. No.: 726,510

[22] Filed: Oct. 7, 1996

[51] Int. Cl.$^6$ .................................................... A61F 13/00
[52] U.S. Cl. ........................... 424/443; 424/448; 424/449
[58] Field of Search .................................. 424/448, 449, 424/443

[56] References Cited

U.S. PATENT DOCUMENTS

| | | | |
|---|---|---|---|
| 3,645,835 | 2/1972 | Hodgson | 161/146 |
| 4,595,001 | 6/1986 | Potter et al. | 128/156 |
| 4,693,776 | 9/1987 | Krampe et al. | 156/327 |
| 4,798,201 | 1/1989 | Rawlings et al. | 128/156 |
| 5,009,224 | 4/1991 | Cole | 128/156 |
| 5,147,698 | 9/1992 | Cole | 428/40 |
| 5,270,358 | 12/1993 | Asmus | 524/55 |
| 5,369,155 | 11/1994 | Asmus | 524/55 |
| 5,531,855 | 7/1996 | Heinecke et al. | 156/252 |

FOREIGN PATENT DOCUMENTS

| | | |
|---|---|---|
| 0 591 898 A1 | 4/1984 | European Pat. Off. . |
| 0 437 944 A1 | 7/1991 | European Pat. Off. . |
| PCT/US84/ 00506 | 10/1984 | WIPO . |
| 88/01878 | 3/1988 | WIPO . |
| 96/08223 | 3/1996 | WIPO . |
| 96/22753 | 8/1996 | WIPO . |

OTHER PUBLICATIONS

BF Goodrich, "Thermoplastic Polyurethane", *Estane,* 1996.

D.G. Davis et al., "New Hydrophilic Polyether–Ester–Amide Block Copolymers", *Antec,* pp. 622–627, 1992.

Fischer, "Polyether Block Amide TPEs", *Medical Device Technology,* pp. 32–36, Sep. 1994.

*Primary Examiner*—D. Gabrielle Brouillette
*Attorney, Agent, or Firm*—Robert W. Sprague

[57] ABSTRACT

An adhesive dressing includes an adhesive composition in the form of a substantially continuous layer on at least a portion of a conformable backing in which the adhesive composition and the backing are selected such that the adhesive dressing has an Inverted Buffered Saline Moisture Vapor Transmission Rate of at least about 9000 g/m$^2$/24 hrs.

15 Claims, No Drawings

MOISTURE-REGULATING ADHESIVE DRESSING

BACKGROUND OF THE INVENTION

The invention relates to regulating the amount of moisture associated with a wound site during the healing process.

Wound dressings are designed to adhere to a patient's skin in order to protect an underlying wound during the healing process. To be effective, such dressings must conform and adhere to moist skin without sticking to the wound surface. In addition, such dressings must control the amount of moisture associated with the wound site.

SUMMARY OF THE INVENTION

The invention features an adhesive dressing that includes an adhesive composition in the form of a substantially continuous layer on at least a portion of a conformable backing in which the adhesive composition and the backing are selected such that said adhesive dressing has an Inverted Buffered Saline Moisture Vapor Transmission Rate of at least about 9000 $g/m^2/24$ hrs.

In preferred embodiments, the adhesive dressing has an Inverted Buffered Saline Moisture Vapor Transmission Rate of at least about 10,000 $g/m^2/24$ hrs, more preferably at least about 12,000 $g/m^2/24$ hrs. Particularly preferred are adhesive dressings having an Inverted Buffered Saline Moisture Vapor Transmission Rate of between about 9000 and about 16,000 $g/m^2/24$ hrs.

The adhesive dressing preferably has an Inverted Buffered Saline Moisture Vapor Transmission Rate that is at least about four times greater than the Inverted Water Moisture Vapor Transmission Rate (as measured according to ASTM E-96-80). In some preferred embodiments, the adhesive dressing has an Inverted Water Moisture Vapor Transmission Rate of no greater than about 3000 $g/m^2/24$ hrs.

A preferred adhesive composition includes the reaction product of: (a) an acrylic or methacrylic acid ester of a non-tertiary alcohol having between 4 and 14 carbon atoms, inclusive; (b) a hydrophilic, ethylenically unsaturated monomer; and (c) at least 15 parts by weight of an ethylenically unsaturated monomer having one or more carboxylic acid groups. By "hydrophilic" it is meant that the monomer has a high affinity for water. Examples of preferred hydrophilic monomers include an acrylate or methacrylate-terminated polyalkylene glycol. An example of a preferred ethylenically unsaturated monomer having one or more carboxylic acid groups is acrylic acid. Examples of preferred acrylic or methacrylic acid esters include iso-octyl acrylate, 2-ethylhexyl acrylate, n-butyl acrylate, or a combination thereof. A particularly preferred adhesive composition includes the reaction product of iso-octyl acrylate, an acrylate or methacrylate-terminated polyalkylene glycol, and acrylic acid.

The backing preferably includes a thermoplastic polyurethane. It preferably has an Inverted Buffered Saline Moisture Vapor Transmission Rate of at least about 9000 $g/m^2/24$ hrs. It may include one or more layers of material which may be the same as, or different from, each other. Moreover, the backing preferably has a wet tensile strength of at least about $20 \times 10^6 N/m^2$.

The invention provides an adhesive dressing useful for treating wounds which effectively regulates the amount of moisture in contact with the wound underlying the dressing. The moisture vapor transmission rate of the dressing changes in response to changes in the pH of the body fluids associated with the underlying wound. It is thus possible to maintain a moist environment sufficient to prevent the underlying wound from dehydrating without creating pools of liquid that can cause adhesive failure. The dressing also exhibits a high moisture vapor transmission rate while retaining its structural integrity in moist environments. Moreover, the use of a continuous adhesive composition provides improved adhesion to skin relative to dressings featuring patterned adhesive compositions on a backing, and avoids creating channels for fluid leakage.

Other features and advantages of the invention will be apparent from the following description of the preferred embodiments thereof, and from the claims.

DESCRIPTION OF THE PREFERRED EMBODIMENTS

The adhesive dressings feature an adhesive composition provided on a hydrophilic backing in the form of a substantially continuous layer. The dressings are designed to optimize the moisture content of an underlying wound while remaining adhered to skin.

The invention was made possible, in part, by the inventors' discovery of a new method for measuring moisture vapor transmission rate. This method, called the Inverted Buffered Saline Moisture Vapor Transmission Test, measures moisture vapor transmission rate in a slightly alkaline environment (e.g., about pH 7.2 to 7.4) typical of the environment associated with a fresh wound. The method is similar to the Inverted Water Moisture Vapor Transmission Test often used to measure the moisture vapor transmission properties of films, except that it substitutes buffered saline for deionized water. The method thus provides a good indication of the moisture vapor transmission rate requirements of the wound, thereby providing the basis for designing dressings designed to meet these requirements.

As the wound heals, the pH of the wound environment changes. The Inverted Water Moisture Vapor Transmission Test provides a good measure of the moisture vapor transmission rate requirements of the wound at neutral pH.

Using the Inverted Buffered Saline Moisture Vapor Transmission Rate Test and Inverted Water Moisture Vapor Transmission Rate Test as guides, the optimum dressings for wound management are those in which the adhesive composition and the backing are selected such that the dressing exhibits an Inverted Buffered Saline Moisture Vapor Transmission Rate of at least about 9,000 $g/m^2/24$ hrs. and an Inverted Water Moisture Vapor Transmission Rate of no greater than about 3,000 $g/m^2/24$ hrs.

The backing is a conformable, hydrophilic, polymeric material which has a high moisture vapor transmission rate (as measured according to both the Inverted Buffered Saline Moisture Vapor Transmission Rate Test and the Inverted Water Moisture Vapor Transmission Rate Test), yet retains its structural integrity in a moist environment. Preferably, the backing has an Inverted Buffered Saline Moisture Vapor Transmission Rate of at least about 9,000 $g/m^2/24$ hrs, an Inverted Water Moisture Vapor Transmission Rate of at least about 9,000 $g/m^2/24$ hrs., and a wet tensile strength of at least about $20 \times 10^6 N/m^2$.

The backing may include one or more layers of material tailored to achieve the above-described moisture vapor transmission and structural integrity properties. Examples of suitable materials include hydrophilic thermoplastic urethanes commercially available from B.F. Goodrich under the trade designation "Estane™" including, for example, Estane™ 58237 and Estane™ 58245; hydrophilic thermoplastic polyether-amide block copolymers commercially available from ATOCHEM under the trade designation "PEBAX 4011;" and polyether-ester block copolymers.

The adhesive composition is provided on a surface of the backing in the form of a substantially continuous layer. Preferably, it is in the form of a pressure sensitive adhesive. The adhesive composition is selected such that it cooperates with the backing to yield a dressing having the aforementioned moisture vapor transmission characteristics. Preferably, the adhesive composition is a hydrophilic composition having a sufficiently high concentration of acidic groups such that it has a moisture vapor transmission rate that approximates the pH of the wound site underlying the dressing, and changes in response to changes in the pH of the wound site.

A preferred adhesive composition is the reaction product of (a) 50 to 80 parts of an acrylic or methacrylic acid ester of a non-tertiary alcohol having between 4 and 14 carbon atoms, inclusive; (b) 10 to 30 parts by weight of a hydrophilic, ethylenically unsaturated monomer; and (c) at least 15 parts by weight (e.g., 15–25 parts by weight) of an ethylenically unsaturated monomer having one or more carboxylic acid groups.

Examples of suitable acrylic and methacrylic acid ester monomers include esters prepared by reaction with alcohols such a 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl alcohol, 2-ethyl-1-hexanol, 1-decanol, 1-dodecanol, 1-tridecanol, 1-tetradecanol, and the like, as well as combinations thereof. Particularly preferred ester monomers include isooctyl acrylate, 2-ethyl hexyl acrylate, and n-butyl acrylate.

Examples of suitable ethylenically unsaturated hydrophilic monomers include free radically reactive hydrophilic oligomers (a polymer having a low number of repeating units, generally 2 to 20) and/or polymers including poly(alkylene oxides). Other suitable ethylenically unsaturated hydrophilic monomers include macromonomers, e.g., acrylate-terminated poly(ethylene oxide), methacrylate-terminated poly(ethylene oxide), methoxy poly(ethylene oxide) methacrylate, butoxy poly(ethylene oxide) methacrylate, p-vinyl benzyl-terminated poly(ethylene oxide), methoxy poly(ethylene oxide) acrylate, butoxy poly(ethylene oxide) acrylate, poly(ethylene oxide) diacrylate, poly(ethylene oxide) dimethacrylate, and combinations thereof. Particularly preferred ethylenically unsaturated hydrophilic monomers include acrylate and methacrylate esters prepared from mono-hydroxyl-terminated poly(lower alkylene oxides) such as polyethylene and polypropylene glycols commercially available under the trade designation "Carbowax™" from Union Carbide Corp. in a variety of molecular weights (e.g., Carbowax™ 350, Carbowax™ 550, Carbowax™ 750, Carbowax™ 2000, and Carbowax™ 5000). An example of a preferred acrylate-terminated poly(ethylene glycol) is commercially available from Shin-Nakamura Chemical Co., Ltd., Japan, under the designation "NK Ester AM-90G."

Examples of suitable carboxylic acid-containing monomers include acrylic acid, methacrylic acid, itaconic acid, and combinations thereof. The preferred monomer is acrylic acid.

Other useful materials that can be added to the adhesive composition include chain transfer agents for controlling molecular weight (e.g., carbon tetrabromide, mercaptans, or alcohols), tackifiers, plasticizers (e.g., polyethylene glycol, polypropylene glycol, or glycerin), perfumes, deodorants, antioxidants, and pharmacologically active ingredients such as drugs, antibiotics, and anti-microbial agents. The chain transfer agents are added to the monomer mixture. The other materials can be added to the monomer mixture or to the polymerized composition.

The adhesive compositions can be prepared according to a variety of well-known polymerization techniques, including solution, emulsion, and bulk polymerization (e.g., actinic radiation-initiated polymerization as described in Martens et al., U.S. Pat. No. 4,181,752, hereby incorporated by reference). They may be used alone or blended with discrete, crosslinked polymer microspheres as described in a concurrently filed, commonly assigned application in the name of Lucast et al. entitled "Pressure Sensitive Adhesive Articles and Methods for Preparing Same," bearing U.S. Ser. No. 08/726,513, which is hereby incorporated by reference.

The microspheres are prepared via a free radical suspension polymerization process. They may be solid or hollow, and either tacky or tack-free. The tack-free microspheres can be elastomeric or plastic. The microspheres typically have diameters ranging from about 1 micrometer to about 300 micrometers. The amount of microspheres preferably is between about 1% and about 75% by volume, and is selected to yield a blend having a substantially smooth, exposed surface available for adhesion after applying the adhesive composition to the backing.

The invention will now be described further by way of the following examples.

EXAMPLES

Test Procedures
Inverted Water Moisture Vapor Transmission Rate

The moisture vapor transmission rate was measured according to ASTM E-96-80 using a modified Payne cup method. Specifically, a 35 mm diameter sample of 1 mil (0.025 mm) thick material to be tested containing no perforations was cut. The sample was placed between adhesive-containing surfaces of two foil adhesive rings, each having a one inch (2.54 cm) diameter hole. The holes of each ring were carefully aligned. Finger pressure was used to form a foil/sample/foil assembly that was flat, wrinkle-free, and had no void areas in the exposed sample.

A 4 oz. (0.14 kg) glass jar was filled half-way with distilled water. The jar was fitted with a screw-on cap having a 1.50 inch (3.8 cm) diameter hole in the center thereof and with a 1.75 inch (4.45 cm) diameter rubber washer having a 1.12 inch (2.84 cm) diameter hole in its center. The rubber washer was placed on the lip of the jar and the foil/sample assembly was placed on the rubber washer. The lid was then screwed loosely on the jar.

The assembly was placed in a chamber at 100° F. (38° C.) and 20% relative humidity for four hours. The cap was tightened inside the chamber so that the sample was level with the cap (no bulging) and the rubber washer was in proper seating position.

At the end of four hours, the foil/sample assembly was removed from the chamber and weighed immediately to the nearest 0.01 gram (initial weight $W_1$). The assembly was then returned to the chamber for at least 18 hours, after which it was removed and weighed immediately to the nearest 0.01 gram (final weight $W_2$). The moisture vapor transmission rate (MVTR) in grams of water vapor transmitted per square meter of sample area in 24 hours was calculated according to the following formula (where "T" refers to exposure time in hours):

$MVTR = (W_1 - W_2)(4.74 \times 10^4)/T$

Three measurements of each sample were made, and the average value taken. The MVTR values are reported in Table 1 in g/m²/24 hrs.

Inverted Buffered Saline Moisture Vapor Transmission Rate

The procedure is the same as the Inverted Water Moisture Vapor Transmission Rate Test except that phosphate-buffered saline is substituted for distilled water. The MVTR values are reported in Table 1 in g/m²/24 hours.

Example 1

An adhesive composition featuring a pressure sensitive adhesive matrix blended with polymeric microspheres was prepared as follows.

To prepare the microspheres, a monomer mixture was prepared by dissolving 4.8 g of acrylic acid, 2.4 g of Carbowax™ 750 acrylate (polyethylene oxide acrylate) and 1.13 g Lucidol™-70 (70% benzoyl peroxide) in 232.8 g of iso-octyl acrylate. A surfactant solution was prepared by dissolving 0.75 g of sodium dodecyl benzene sulfonate in 360 g of water. The monomer mixture was then added to the surfactant solution, and the resulting mixture emulsified using a Gifford-Wood™ mixer until the droplet size was less than 5 micrometers. The emulsion was charged to a 1 liter baffled reactor, heated to 65° C., degassed with $N_2$, and allowed to react for 8 hours. Microspheres having an average diameter of about 2 micrometers were formed during the reaction period.

The adhesive matrix was prepared according to the procedures described generally in PCT US84/00506 and WP 84/03837 using a monomer mixture containing 70 parts by weight isooctyl acrylate, 15 parts by weight acrylic acid, and 15 parts by weight Carbowax™ 750 acrylate (polyethylene oxide acrylate). The matrix was then blended with the microspheres (30 microspheres per hundred parts matrix) using a Lightening-brand mixer and applied to a release liner made of silicone-coated kraft paper.

Next, a 25 micrometer thick film of Estane™ 58237 thermoplastic polyurethane (B.F. Goodrich Co.) was extruded and laminated to the adhesive composition. The thickness of the adhesive composition was 25 microns (1 mil). A dressing was prepared according to the procedure described in Example 1 of Heinecke et al., U.S. Pat. No. 5,531,855, hereby incorporated by reference to provide a frame delivery system of 6 cm×7 cm or 10 cm×12 cm.

The moisture vapor transmission properties of the dressing were measured and are reported in Table 1.

Example 2

The procedure of Example 1 was followed except that the adhesive composition did not contain any microspheres. The moisture vapor transmission properties of the dressing were measured and are reported in Table 1.

Example 3

The procedure of Example 1 was followed except that the matrix was prepared from a monomer mixture containing 60 parts isooctyl acrylate, 20 parts by weight acrylic acid, and 20 parts by weight Carbowax™ 750 acrylate (polyethylene oxide acrylate). The moisture vapor transmission properties of the dressing were measured and are reported in Table 1.

TABLE 1

MOISTURE VAPOR TRANSMISSION RATE (G/M²/24 HRS)

| EXAMPLE | INVERTED WATER MVTR | INVERTED BUFFERED SALINE MVTR |
|---|---|---|
| 1 | 1540 | 16,000 |
| 2 | 1200 | 9,100 |
| 3 | 2800 | 11,000 |
| ESTANE 58237* | 16,000 | 16,000 |

*Estane ™ 58247 polyurethane backing (25 micrometer thickness without any adhesive composition.

Other embodiments are within the following claims.

What is claimed is:

1. An adhesive dressing comprising an adhesive composition in the form of a substantially continuous layer on at least a portion of a conformable backing consisting of a single layer of material, said adhesive composition comprising the reaction product of a monomer mixture that includes at least 15 parts by weight of an ethylenically unsaturated monomer having one or more carboxylic acid groups, said adhesive composition and said backing being selected such that said adhesive dressing has an Inverted Buffered Saline Moisture Vapor Transmission Rate of at least about 9000 g/m²/24 hrs.

2. The adhesive dressing of claim 1, wherein said adhesive dressing has an Inverted Buffered Saline Moisture Vapor Transmission Rate of at least about 10,000 g/m²/24 hrs.

3. The adhesive dressing of claim 1, wherein said adhesive dressing has an Inverted Buffered Saline Moisture Vapor Transmission Rate of at least about 12,000 g/m²/24 hrs.

4. The adhesive dressing of claim 1, wherein said adhesive dressing has an Inverted Buffered Saline Moisture Vapor Transmission Rate of between about 9000 and about 16,000 g/m²/24 hrs.

5. The adhesive dressing of claim 1, wherein said adhesive dressing has an Inverted Water Moisture Vapor Transmission Rate of no greater than about 3000 g/m²/24 hrs.

6. The adhesive dressing of claim 1, wherein said dressing has an Inverted Buffered Saline Moisture Vapor Transmission Rate that is at least about four times greater than the Inverted Water Moisture Vapor Transmission Rate.

7. The adhesive dressing of claim 1, wherein said adhesive composition comprises the reaction product of:

(a) an acrylic or methacrylic acid ester of a nontertiary alcohol having between 4 and 14 carbon atoms, inclusive;

(b) a hydrophilic, ethylenically unsaturated monomer; and (c) at least 15 parts by weight of an ethylenically unsaturated monomer having one or more carboxylic acid groups.

8. The adhesive dressing of claim 7, wherein said hydrophilic monomer comprises an acrylate or methacrylate-terminated polyalkylene glycol.

9. The adhesive dressing of claim 7, wherein said ethylenically unsaturated monomer having one or more carboxylic acid groups comprises acrylic acid.

10. The adhesive dressing of claim 7, wherein said acrylic or methacrylic acid ester comprises iso-octyl acrylate, 2-ethyl hexyl acrylate, n-butyl acrylate, or a combination thereof.

11. The adhesive dressing of claim 1, wherein said adhesive composition comprises the reaction product of iso-octyl acrylate, an acrylate or methacrylate-terminated polyalkylene glycol, and acrylic acid.

12. The adhesive dressing of claim 1, wherein said backing comprises a thermoplastic polyurethane.

13. The adhesive dressing of claim 1, wherein said backing has an Inverted Buffered Saline Moisture Vapor Transmission Rate of at least about 9000 g/m²/24 hrs.

14. The adhesive dressing of claim 1, wherein said backing comprises a plurality of layers.

15. The adhesive dressing of claim 1, wherein said backing has a wet tensile strength of at least about $20 \times 10^6 \text{N/m}^2$.

* * * * *